United States Patent [19]

Bauer et al.

[11] Patent Number: 4,686,303

[45] Date of Patent: Aug. 11, 1987

[54] PROCESS FOR THE PREPARATION OF DIARYL SULPHIDES

[75] Inventors: Wolfgang Bauer, Maintal; Manfred Langer, Frankfurt am Main; Winfried Sperling, Nidderau, all of Fed. Rep. of Germany

[73] Assignee: Cassella Aktiengesellschaft, Frankfurt am Main, Fed. Rep. of Germany

[21] Appl. No.: 879,081

[22] Filed: Jun. 26, 1986

[30] Foreign Application Priority Data

Jul. 5, 1985 [DE] Fed. Rep. of Germany ....... 3524095

[51] Int. Cl.$^4$ ................. C07C 149/30; C07C 149/34; C07C 149/40
[52] U.S. Cl. ...................................... 560/18; 562/432; 568/44; 568/53; 568/56; 568/58
[58] Field of Search .......................... 560/18; 562/432; 568/44, 53, 56, 58

[56] References Cited

U.S. PATENT DOCUMENTS

| | | | |
|---|---|---|---|
| 1,769,423 | 7/1930 | Eder | 562/432 |
| 3,514,480 | 5/1970 | Fields | 562/432 |
| 4,493,802 | 1/1985 | Jundicke | 562/432 |

*Primary Examiner*—Michael L. Shippen
*Attorney, Agent, or Firm*—Connolly & Hutz

[57] ABSTRACT

A process for preparation of diaryl sulphides by reaction of an aromatic diazonium salt in an alkaline medium with arenethiol is catalyzed by a non-metallic solid, such as charcoal, silica gel or aluminium oxide, having a specific surface of greater than or equal to 0.02 $m^2/cm^3$.

15 Claims, No Drawings

PROCESS FOR THE PREPARATION OF DIARYL SULPHIDES

The present invention relates to a process for the preparation of diaryl sulphides by reaction of an aromatic diazonium salt with an arenethiol in alkaline medium in the presence of a catalyst.

In one of the most usual processes for the preparation of diaryl sulphides, the solution of an aromatic diazonium salt is reacted with an arenethiol in alkaline solution (cf. Houben-Weyl "Methoden der Organischen Chemie", G. Thieme Verlag, Stuttgart, 4th edition (1955), volume IX, 116–117). The reaction takes the following course:

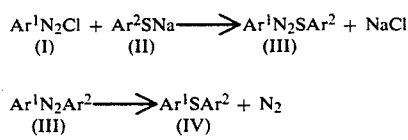

$$Ar^1N_2Cl + Ar^2SNa \longrightarrow Ar^1N_2SAr^2 + NaCl \qquad 1.$$
$$\phantom{Ar^1N_2Cl + }(I) \phantom{ + }(II) \phantom{\longrightarrow}(III)$$

$$Ar^1N_2Ar^2 \longrightarrow Ar^1SAr^2 + N_2 \qquad 2.$$
$$\phantom{Ar^1N_}(III) \phantom{\longrightarrow}(IV)$$

In the first stage here, the diaryldiazo sulphides III are formed initially, which can sometimes decompose explosively, even in aqueous solution.

To avoid the safety risk caused by the possible explosive decomposition of the diaryldiazo sulphides III, two different methods of carrying out the reaction are known (cf. Houben-Weyl loc. cit.).

In the first method, the diaryldiazo sulphide is decomposed only shortly after its formation by allowing the diazonium salt solution to run slowly into the alkaline solution of the thiol, which has been warmed to over 70° C., with vigorous stirring.

The disadvantage of this method is the decomposition reaction of the arenediazonium salts, which occurs at elevated temperature to give phenols, causing a marked reduction in the yield of diaryl sulphides. Furthermore, considerable environmental pollution or pollution of the waste water from the plant by phenolic compounds, which have to be removed by cost-intensive purification methods, also results.

According to the second method, the reaction is carried out at lower temperature and in the presence of copper powder which catalyses the decomposition of the diaryldiazo sulphide of the formula III. Although the competing formation of phenol is forced back or suppressed in this method, problems do occur caused by handling copper and waste water pollution by copper salts.

The object of the present invention was to provide a process for the preparation of diaryl sulphides which avoids the disadvantages of the previous processes, in particular achieves better yields and has no ecological and safety problems.

This object is surprisingly achieved by employing a nonmetallic solid with a specific surface of greater than or equal to 0.02 m$^2$/cm$^3$, preferably of greater than or equal to 0.06 m$^2$/cm$^3$, as catalyst in the reaction of an aromatic diazonium salt with an arenethiol in alkaline medium.

Such non-metallic solids with a specific surface of greater than or equal to 0.02 m$^2$/cm$^3$, preferably of greater than or equal to 0.06 m$^2$/cm$^3$, which are suitable as catalysts for the process according to the invention are, for example, finely divided non-metallic solids with particle diameters of less than or equal to 0.3 mm, preferably of less than or equal to 0.1 mm. For example, all water-insoluble synthetic or natural substances which are employed as adsorbents in industrial adsorption processes or in adsorption chromatography are suitable, thus, for example: activated charcoals, animal charcoals, bone charcoals, silicates and aluminium silicates, such as, for example, silicon dioxide (silica gel), diatomaceous earth, bleaching earths, bentonites, montmorillonite, aluminium oxides, bauxites, talc, glass powder, and molecular sieves. Furthermore, for example, water-insoluble oxides and salts, for example carbonates, silicates or sulphates of alkaline earth metals, zinc and the like, such as, for example, magnesium oxide, magnesium carbonate, magnesium silicate, zinc carbonate, calcium carbonate, barium sulphate, etc., are suitable. Some of these substances, normally used as adsorbents, have high specific surfaces of normally 100 m$^2$/cm$^3$ and more. If a high inner surface is present, they can be employed as a catalyst in the process according to the invention not only in finely divided form, but also in granular form. This is possible for activated charcoal, for example, which is commercially available as powdered charcoal and as so-called granular charcoal and pelleted charcoal with grain sizes of, for example, up to 4 mm.

Finely divided substances which, for example, are normally used as filter auxiliaries can also be used in the process according to the invention. Typical perlite filter auxiliaries possess, for example, specific surfaces of about 0.35 m$^2$/cm$^3$. Suitable filter auxiliaries are commercially available under various names, such as, for example, Celite ® and Corlite ®.

However, other solids, such as, for example, synthetic or natural ion exchangers, in particular cation exchangers, can also be used as the catalyst in the process according to the invention. The non-metallic solids employed as catalyst should be insoluble or inert under the reaction conditions.

The aromatic diazonium salts required in the process according to the invention as a starting material are prepared in a manner known per se by diazotization of an aromatic amine of the formula V $$Ar^1NH_2 \qquad (V)$$

in mineral acid medium. The aryl radical Ar$^1$ here represents an optionally monosubstituted or polysubstituted aryl radical, in particular an optionally monosubstituted or polysubstituted phenyl radical. The phenyl radical can, for example, be monosubstituted or polysubstituted by alkyl, in particular with 1 to 4 C-atoms, alkoxy, in particular with 1 to 4 C-atoms, halogen, in particular chlorine, bromine or fluorine, carboxyl, alkoxycarbonyl, in particular with 1 to 4 C-atoms in the alkoxy radical, and/or nitro. As a rule, however, only one nitro group is present in a polysubstitution.

Suitable amines of the formula V are, for example: aniline, 2-, 3- or 4-methylaniline, 2-, 3- or 4-ethylaniline, 2-, 3- or 4-isopropylaniline, 2-, 3- or 4- tert.butylaniline, 2-, 3- or 4-methoxyaniline, 2-, 3- or 4-propoxyaniline, 2-, 3- or 4-isobutoxyaniline, 2-, 3- or 4-chloro-, bromo- or fluoroaniline, 2-,3-, 2,4-, 2,5- or 2,6-dichloroaniline, 2-chloro-4-bromoaniline, 2-, 3- or 4-aminobenzoic acid, the methyl, ethyl, isopropyl or butyl esters of 2-, 3- or 4-aminobenzoic acid, 4-, 5- or 6-chloro-2-aminobenzoic acid, 3-, 4-, 5- or 6-fluoro-2-aminobenzoic acid, 2-amino -4,5-dimethoxybenzoic acid or 2-amino-4,5-diethoxybenzoic acid.

The solution of the aromatic diazonium salt which has been prepared in a known fashion is, as a rule, immediately processed further and reacted, in an alkaline medium, with the arenethiol in the presence of a non-metallic solid with a specific surface of greater than or equal to 0.02 m²/cm³.

Normally, the arenethiol and the catalyst here are initially introduced in an alkaline medium and the solution of the arenediazonium salt is metered in slowly.

The reaction is carried out in an aqueous medium. The reaction medium is usually water; however, water-miscible solvents, for example mono- or polyalcohols, particularly those with 1 to 4 C-atoms, such as, for example, methanol, isopropanol, butanol, or isobutanol, or sparingly water-miscible solvents such as, for example, methylene chloride, toluene or chlorobenzene, can be present in addition to the water. As arenethiol, compounds of the general formula VI $$Ar^2SH \quad (VI)$$

are employed, the aryl radical $Ar^2$ representing an optionally monosubstituted or polysubstituted aryl radical, in particular an optionally monosubstituted or polysubstituted phenyl radical. The phenyl radical can, for example, be monosubstituted or polysubstituted by alkyl, in particular with 1 to 4 C-atoms, alkoxy, in particular with 1 to 4 C-atoms, by halogen, in particular chlorine, bromine, or fluorine, and/or nitro. However, as a rule, only one nitro group is present here in a polysubstitution.

The radicals $Ar^1$ and $Ar^2$ can also be identical.

Suitable arenethiols of the formula VI are, for example, benzenethiol, 2-, 3- or 4-toluenethiol, 2-, 3- or 4-ethylbenzenethiol, 2-, 3- or 4-isopropylbenzenethiol, 2-, 3- or 4-chlorobenzenethiol, 2-, 3- or 4-bromobenzenethiol, 2-, 3- or 4-fluorobenzenethiol, 2-, 3- or 4-nitrobenzenethiol, 2-, 3- or 4-methoxybenzenethiol, 2-, 3- or 4-propoxybenzenethiol, 2,3-, 2,4-, 2,5-dichlorobenzenethiol, 4-chloro-2,5-dimethylbenzenethiol or 4-chloro-2,5- diethylbenzenethiol.

The arenethiol of the formula VI is converted to the corresponding alkali metal salt in alkaline medium. To start the alkaline reaction, a suitable alkali, particularly an alkali metal hydroxide, is added to the aqueous medium. Suitable alkali metal hydroxides are, for example, lithium hydroxide, sodium hydroxide and/or potassium hydroxide, sodium hydroxide being preferred among these for reasons of cost.

Sufficient alkali is added to the aqueous reaction medium so that the entire reaction can be carried out in the alkaline pH range, in particular in a pH range above 8, preferably in the pH range from 9 to 14.

The reaction is normally carried out in a temperature range of −10° C. to 50° C., preferably in the temperature range from 0° to 20° C., and very particularly preferably in the temperature range from 2° to 10° C.

As a rule, a molar ratio of 1: (1 to 1.05) is observed in the reaction between the arenethiol of the formula VI and the aromatic diazonium salt. Normally, 5 to 60 g of the catalyst used according to the invention are employed per mol of the aromatic diazonium salt. Greater amounts of catalyst do not usually bring any further improvement. Preferably, 10 to 50 g, very particularly preferably 20 to 40 g, of catalyst are employed per mol of the aromatic diazonium salt.

Preferred catalysts are activated charcoal, silica gel and aluminium oxide. Mixtures of different catalysts can also be used. The catalyst is separated off, for example filtered off, after the reaction is completed, and the reaction mixture is worked up in a known fashion.

A surfactant, known per se, for example a non-ionogenic surfactant or anionic surfactant, or an anti-foam agent or foam inhibitor can be added to the reaction mixture to ensure better distribution of the components and to prevent formation of foam during the nitrogen development. Mixtures of several of these substances can also be added. It is expedient to add these agents before the start of the actual reaction.

The process according to the invention offers several advantages over the prior art. For example, the decomposition of the diaryldiazo sulphide intermediate with evolution of nitrogen starts at a low temperature, whereby formation of phenols is avoided. The yield of diaryl sulphides of the formula V is significantly greater as compared with the method carried out without catalyst. Environmental pollution by heavy metals or heavy metal salts does not occur. Furthermore, pollution of the waste water from the plant by phenolic compounds, which are toxic or not readily biodegradable, is significantly reduced by the procedure according to the invention.

The discovery that the reaction between an aromatic diazonium salt and an arenethiol is catalysed in alkaline medium by non-metallic solids with a specific surface of greater than or equal to 0.02 m²/cm³, such as, for example, activated charcoals, molecular sieves, ion exchangers, silica gel etc., must be described as extremely surprising, since it had previously to be assumed that reactions, such as the Sandmeyer reaction, which proceed by replacement of the diazonium group are only catalysed by metals, in particular copper, and soluble metal salts, in particular copper sulphate, the metal or metal ion somehow intervening in the course of the reaction, for example by formation of complexes.

The diaryl sulphides of the formula IV $$Ar^1{-}S{-}Ar^2 \quad (IV)$$

in which $Ar^1$ and $Ar^2$ have the meaning already described, which can be prepared by the process according to the invention, are useful intermediate products for various areas of application, for example for the preparation of thioxanthone derivatives, which, amongst other things, are important in the pharmaceuticals industry or as photosensitizers for coatings which harden under UV light.

EXAMPLE 1

144 g of 2-aminobenzoic acid (anthranilic acid) in a mixture of 1.5 of water and 181 ml of 32% strength hydrochloric acid are diazotized with a solution of 74.5 g of sodium nitrite in 200 ml of water at 0° to 5° C.

After removal of the excess nitric acid using amidosulphonic acid, the resulting solution of the diazonium salt is metered at 3° to 8° C. into a well-stirred mixture of 144.6 g of 4-chlorothiophenol and 35 g of activated charcoal (specific surface according to BET of 750 m²/g) in 5 of water and 200 ml of 10N sodium hydroxide solution. Evolution of nitrogen begins immediately. The mixture is further stirred for 2 hours at 3° to 8° C. and 1 hour at 20° C. and the catalyst is subsequently filtered off. The alkaline reaction solution is adjusted to pH1 using 200 ml of 10N hydrochloric acid, the reaction product precipitating in crystalline form. After filtration, washing of the paste until neutral and drying, 245.5 g of 2-carboxyphenyl 4-chlorophenyl sulphide of 93% purity, corresponding to 228 g of 100% pure 2-carboxyphenyl 4-chlorophenyl sulphide (86% of theory, relative to 4-chlorothiophenol).

2-chlorothioxanthone can be obtained in good quality and yield by means of known cyclization from the crude material which is obtained.

COMPARISON EXAMPLE

The solution of the diazonium salt of 2-aminobenzoic acid, prepared as specified in Example 1, is added to a mixture of 144.6 g of 4-chlorothiophenol, 200 ml of 10N sodium hydroxide solution and 1 of water, a reaction temperature of 50° C. being necessarily maintained in order to initiate evolution of nitrogen and to ensure immediate decomposition of the diaryldiazo sulphide intermediate which is an explosion hazard. The mixture is stirred for 2 hours, the 4,4'-dichlorodiphenyldisulphide (61 g after drying) is filtered off, and the reaction product is isolated, in analogous fashion to Example 1, by acidification of the alkaline filtrate to pH 1 using 10N hydrochloric acid. Yield after drying: 188 g.

2-carboxyphenyl 4-chlorophenyl sulphide content 72%. Yield in % of theory: 51%.

EXAMPLE 2

In a repetition of Example 1, the activated charcoal is replaced by 35 g of a conventional commercial perlite filter auxiliary with a specific surface of about 0.35 m$^3$/cm$^3$. In addition 3 ml of a conventional commercial anti-foam agent ("Entschäumer 7800 neu" from Bayer AG, Leverkusen) are added to the initially introduced mixture.

Along with a very good space-time yield, a very good product yield of 86% of 2-carboxyphenyl 4-chlorophenyl sulphide is obtained.

Examples 3 to 19 which follow are carried out in analogous fashion to Examples 1 or 2. In each case here, the starting materials are indicated under (a) and (b), the catalyst under (c), the solvent under (d) and the yield of final product under (e).

EXAMPLE 3

(a) 2-aminobenzoic acid
(b) 4-chlorobenzenethiol
(c) silica gel
(d) water
(e) 85% of theory of 2-carboxyphenyl 4-chlorophenyl sulphide.

EXAMPLE 4

(a) 2-aminobenzoic acid
(b) 4-chlorobenzenethiol
(c) aluminium oxide, specific surface according to BET of 100 m$^2$/g
(d) water
(e) 84% of theory of 2-carboxyphenyl 4-chlorophenyl sulphide.

EXAMPLE 5

(a) 2-aminobenzoic acid
(b) 4-chlorobenzenethiol
(c) montmorillonite
(d) water
(e) 86% of theory of 2-carboxyphenyl 4-chlorophenyl sulphide.

EXAMPLE 6

(a) 2-aminobenzoic acid
(b) 4-chlorobenzenethiol
(c) zeolite
(d) water
(e) 85% of theory of 2-carboxyphenyl 4-chlorophenyl sulphide.

EXAMPLE 7

(a) 2-aminobenzoic acid
(b) benzenethiol
(c) activated charcoal, specific surface according to BET of 750 m$^2$/g
(d) water
(e) 94% of theory of phenyl 2-carboxyphenyl sulphide.

EXAMPLE 8

(a) 2-aminobenzoic acid
(b) 4-methylbenzenethiol
(c) activated charcoal, specific surface according to BET of 750 m$^2$/g
(d) water
(e) 86% of theory of 2-carboxyphenyl 4-methylphenyl sulphide.

EXAMPLE 9

(a) 2-aminobenzoic acid
(b) 4-bromobenzenethiol
(c) activated charcoal, specific surface according to BET of 1400 m$^2$/g
(d) water
(e) 87% of theory of 2-carboxyphenyl 4-bromophenyl sulphide.

EXAMPLE 10

(a) 2-aminobenzoic acid
(b) 4-fluorobenzenethiol
(c) activated charcoal, specific surface according to BET of 750 m$^2$/g
(d) water
(e) 90% of theory of 2-carboxyphenyl 4-fluorophenyl sulphide.

EXAMPLE 11

(a) 2-aminobenzoic acid
(b) 4-chloro-2,5-dimethylbenzenethiol
(c) activated charcoal, specific surface according to BET of 750 m$^2$/g
(d) water
(e) 84% of theory of 2-carboxyphenyl 4-chloro-2,5-dimethylphenyl sulphide.

EXAMPLE 12

(a) 2-aminobenzoic acid
(b) 4-chlorobenzenethiol
(c) strongly acidic ion exchanger ®Lewatit SC 104 from Bayer AG
(d) water
(e) 77% of theory of 2-carboxyphenyl 4-chlorophenyl sulphide .

EXAMPLE 13

(a) 2-aminobenzoic acid
(b) 4-chlorobenzenethiol
(c) glass powder (diameter 7.5 to 33 μm)
(d) water
(e) 80% of theory of 2-carboxyphenyl 4-chlorophenyl sulphide.

EXAMPLE 14

(a) 2-amino-4-chlorobenzoic acid

(b) benzenethiol
(c) activated charcoal, specific surface according to BET of 750 m$^2$/g
(d) water
(e) 88% of theory of phenyl 2-carboxy-5-chlorophenyl sulphide.

EXAMPLE 15

(a) 2-amino-4-fluorobenzoic acid
(b) benzenethiol
(c) activated charcoal, specific surface according to BET of 750 m$^2$/g
(d) water
(e) 87% of theory of phenyl 2-carboxy-5-fluorophenyl sulphide.

EXAMPLE 16

(a) 2-amino-4-nitrobenzoic acid
(b) benzenethiol
(c) silica gel
(d) water
(e) 80% of theory of phenyl 2-carboxy-5-nitrophenyl sulphide.

EXAMPLE 17

(a) aniline
(b) benzenethiol
(c) activated charcoal, specific surface according to BET of 750 m$^2$/g
(d) water/toluene (weight ratio: 2:1)
(e) 84% of theory of diphenyl sulphide

EXAMPLE 18

(a) aniline
(b) benzenethiol
(c) activated charcoal, specific surface according to BET of 750 m$^2$/g
(d) water/chlorobenzene (weight ratio: 2:1)
(e) 82% of theory of diphenyl sulphide

EXAMPLE 19

(a) 4-aminobenzoic acid
(b) benzenethiol
(c) activated charcoal, specific surface according to BET of 750 m$^2$/g
(d) water/ethanol (weight ratio: 4:1)

(e) 81% of theory of phenyl 2-carboxyphenyl sulphide.

What is claimed is:

1. In the process for preparation of diaryl sulphides by reaction of an aromatic diazonium salt in alkaline medium with an arenethiol in the presence of a catalyst, the improvement comprises said catalyst being a non-metallic solid with a specific surface of greater than or equal to 0.02 m$^2$/cm$^3$.

2. The process as claimed in claim 1 wherein the solid catalyst has a specific surface of greater than or equal to 0.06 m$^2$/cm$^3$.

3. The process as claimed in claim 1 wherein the solid catalyst is in finely divided form with a particle diameter of less than or equal to 0.3 mm.

4. The process as claimed in claim 3 wherein the particle diameter is 0.1 mm or less.

5. The process as claimed in claim 1 wherein the reaction is carried out at pH values of greater than 8.

6. The process as claimed in claim 5 wherein the pH value is from 9 to 14.

7. The process as claimed in claim 1 wherein the reaction is carried out in the temperature range of $-10°$ to $50°$ C.

8. The process as claimed in claim 7 wherein the reaction temperature is from $0°$ to $20°$ C.

9. The process as claimed in claim 7 wherein the reaction temperature is from $2°$ to $10°$ C.

10. The process as claimed in claim 1 wherein 5 to 60 grams of non-metallic solid catalyst are employed per mol of aromatic diazonium salt.

11. The process as claimed in claim 10 wherein the amount of non-metallic solid catalyst is 10 to 50 grams per mol of diazonium salt.

12. The process as claimed in claim 10 wherein the amount of non-metallic solid catalyst is 20 to 40 grams per mol of diazonium salt.

13. The process as claimed in claim 1 wherein the non-metallic solid catalyst is activated charcoal, silica gel or aluminium oxide.

14. The process as claimed in claim 1 wherein the arenethiol and the solid are initially introduced in alkaline medium and a solution of the aromatic diazonium salt is metered in.

15. The process as claimed in claim 1 wherein the reaction is carried out in the presence of an anti-foam agent or a foam inhibitor.

* * * * *